United States Patent
Majeed et al.

(10) Patent No.: US 7,160,562 B2
(45) Date of Patent: Jan. 9, 2007

(54) COMPOSITIONS AND METHODS CONTAINING NATURAL COMPOUNDS FROM NONCONVENTIONAL SOURCES THAT ARE USEFUL IN MAINTAINING NORMAL BLOOD SUGAR LEVELS

(75) Inventors: Muhammed Majeed, Piscataway, NJ (US); Subbalakshmi Prakash, Piscataway, NJ (US); Shipra Roy, Bhopal (IN); Venu Agarwal, Bhopal (IN)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 10/709,726

(22) Filed: May 25, 2004

(65) Prior Publication Data

US 2006/0003035 A1    Jan. 5, 2006

(51) Int. Cl.
*A16K 36/00* (2006.01)

(52) U.S. Cl. .................................. 424/773; 424/725

(58) Field of Classification Search ................ 424/773, 424/725
See application file for complete search history.

(56) References Cited

FOREIGN PATENT DOCUMENTS

JP        2000247829 A    *    9/2000

* cited by examiner

*Primary Examiner*—Christopher Tate
*Assistant Examiner*—S. B. McCormick-Ewoldt

(57) ABSTRACT

The invention describes compositions and methods containing nonconventional plant materials, and more particularly the species *Flemingia macrophylla* and *Careya arborea*, that help to maintain normal blood sugar levels in humans and animals. The method of preparation of such compositions and methods of quantifying active principles therein are also described. A Metformin-like compound were found to be the active hypoglycemic principle in *Flemingia macrophylla* and *Careya arborea* root bark. The compositions of the invention were found to be safe for therapeutic use.

1 Claim, 11 Drawing Sheets

Blood glucose levels of the groups at different time intervals in the study with Flemingia macrophylla (bar graph)

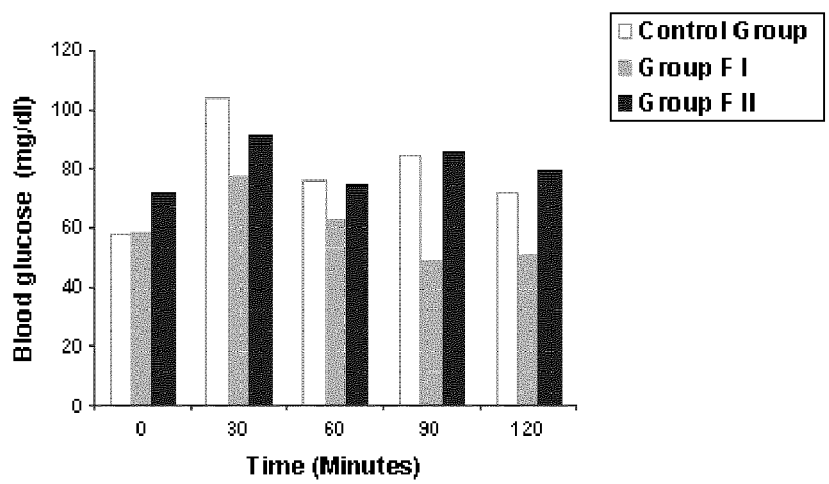
Figure 1: Blood glucose levels of the groups at different time intervals in the study with Flemingia macrophylla (bar graph)

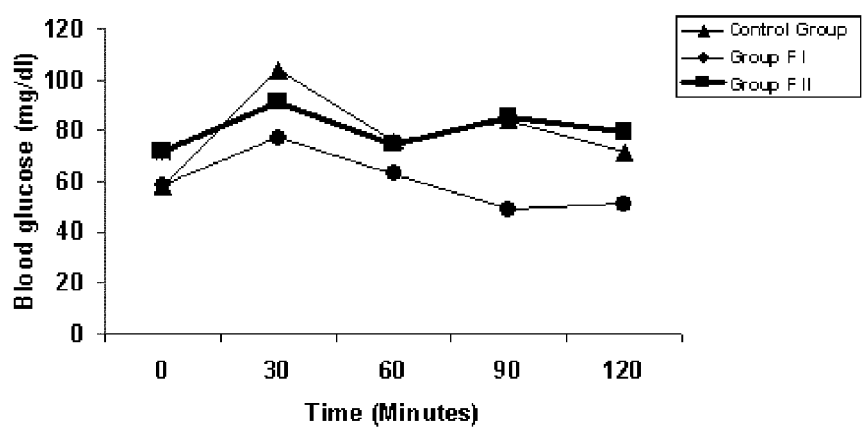
Figure 2: Blood glucose levels of the groups at different time intervals in the study with Flemingia macrophylla (line graph).

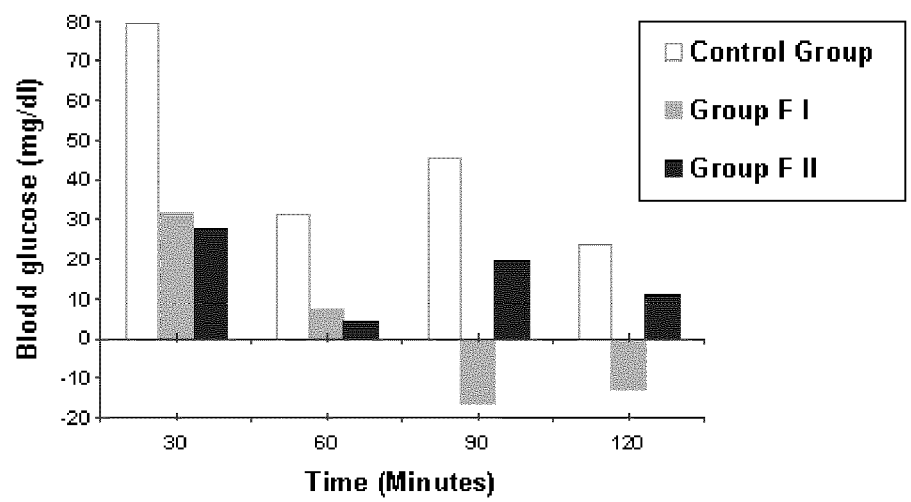
Figure 3: Percent rise in blood glucose levels of the groups at different time intervals in the study with Flemingia macrophylla (bar graph)

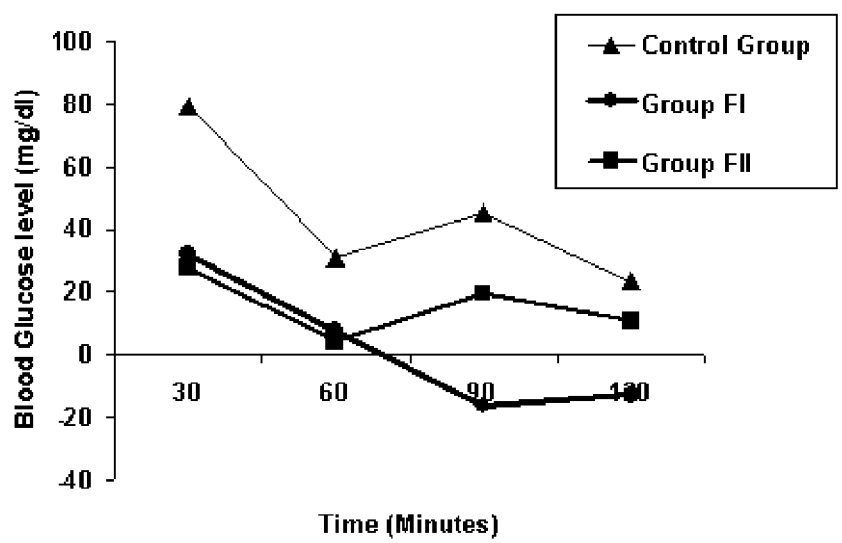
Figure 4 : Percent increase in blood glucose levels of the groups at different time intervals in the study with Flemingia macrophylla (line graph)

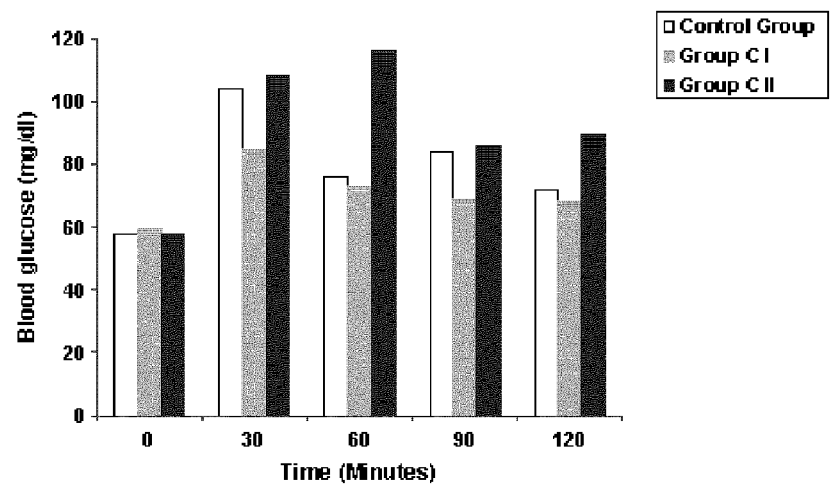
Figure 5 : Blood glucose levels of the groups at different time intervals in the study with Careya arborea (bar graph).

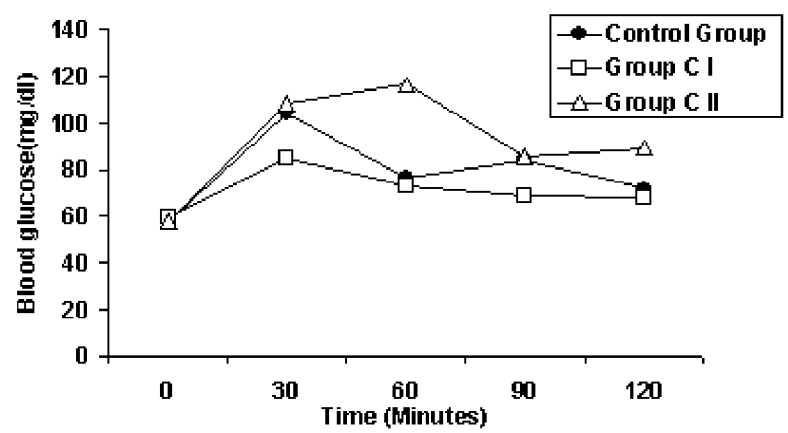
Figure 6: Blood glucose levels of the groups at different time intervals in the study with Careya arborea (line graph)

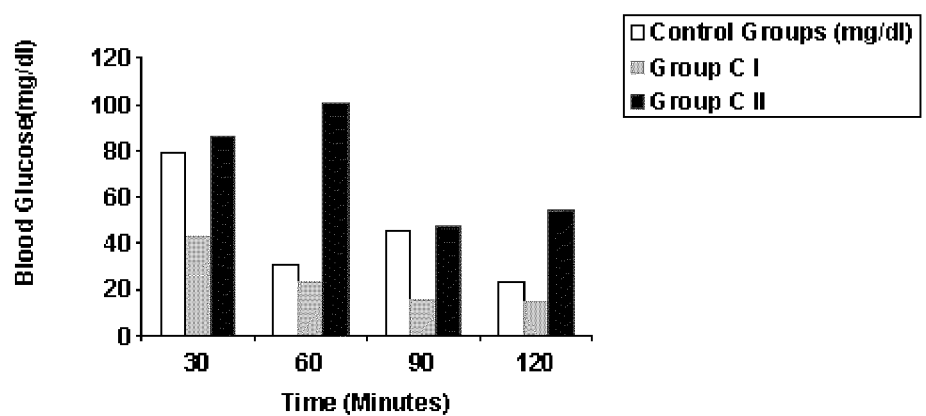
Figure 7: Percent rise in blood glucose levels of the groups at different time intervals in the study with Careya arborea. (bar graph)

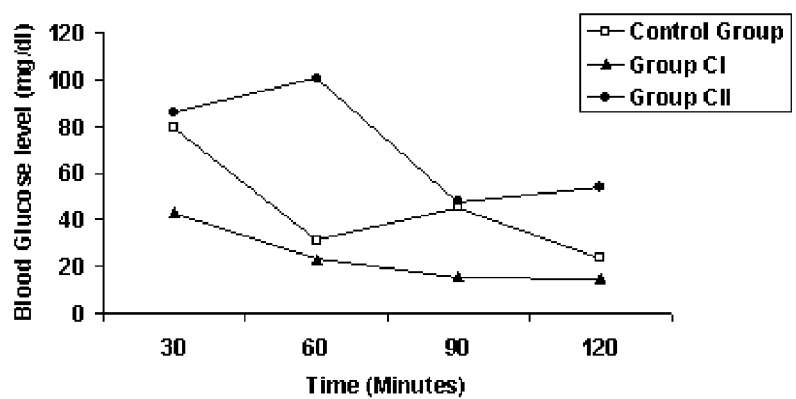
Figure 8 : Percent rise in blood glucose levels of the groups at different time intervals in the study with Careya arborea (line graph).

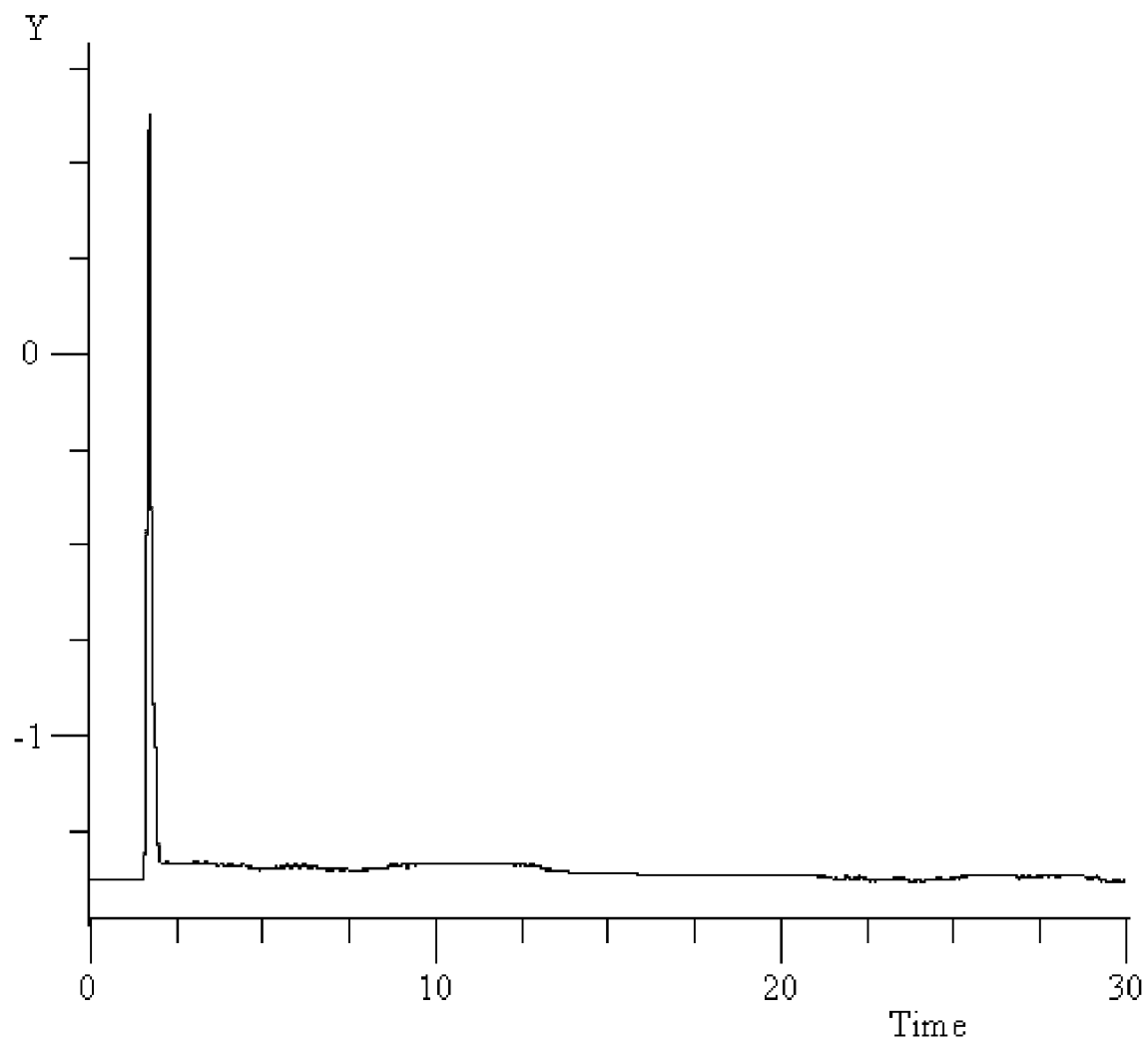
Figure 9: HPLC chromatogram of standard metformin hydrochloride

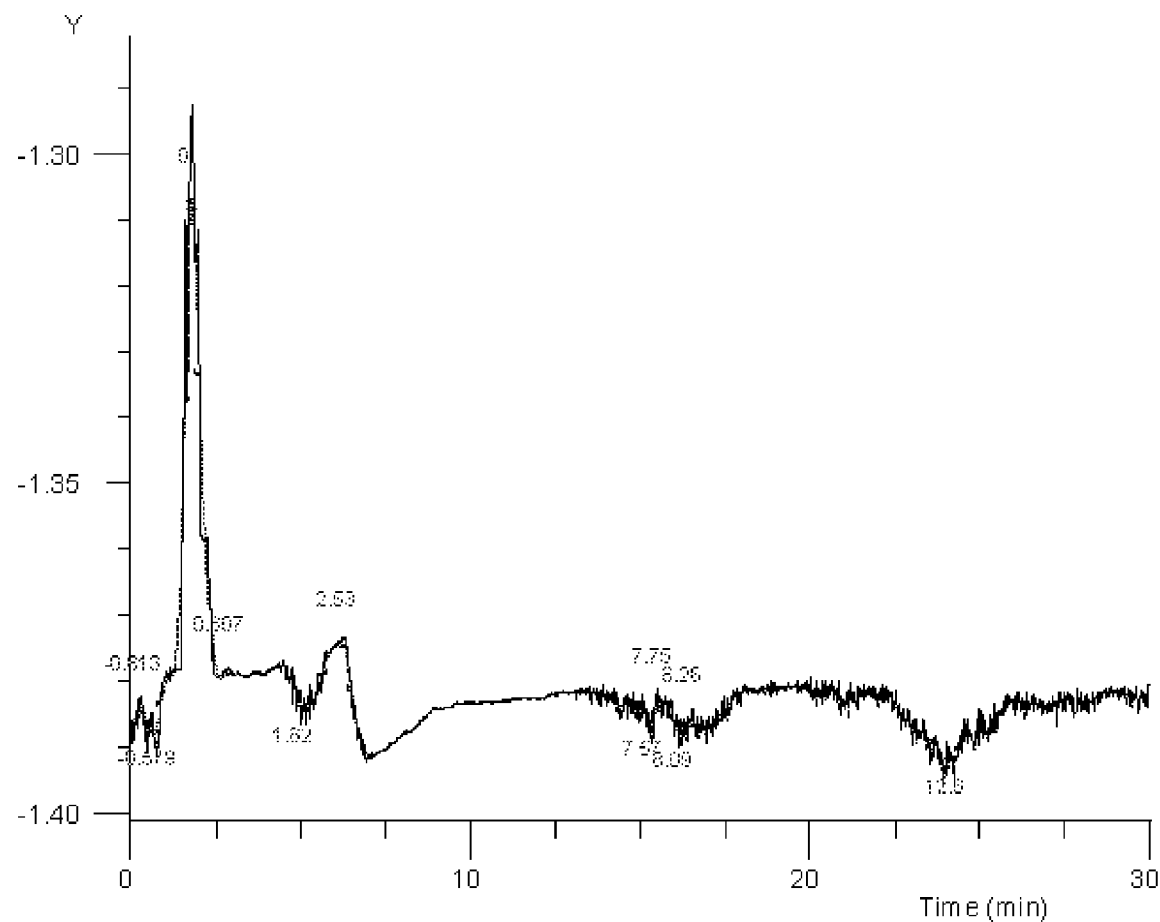
Figure 10: HPLC chromatogram of the aqueous extract of the root covering of Flemingia macrophylla

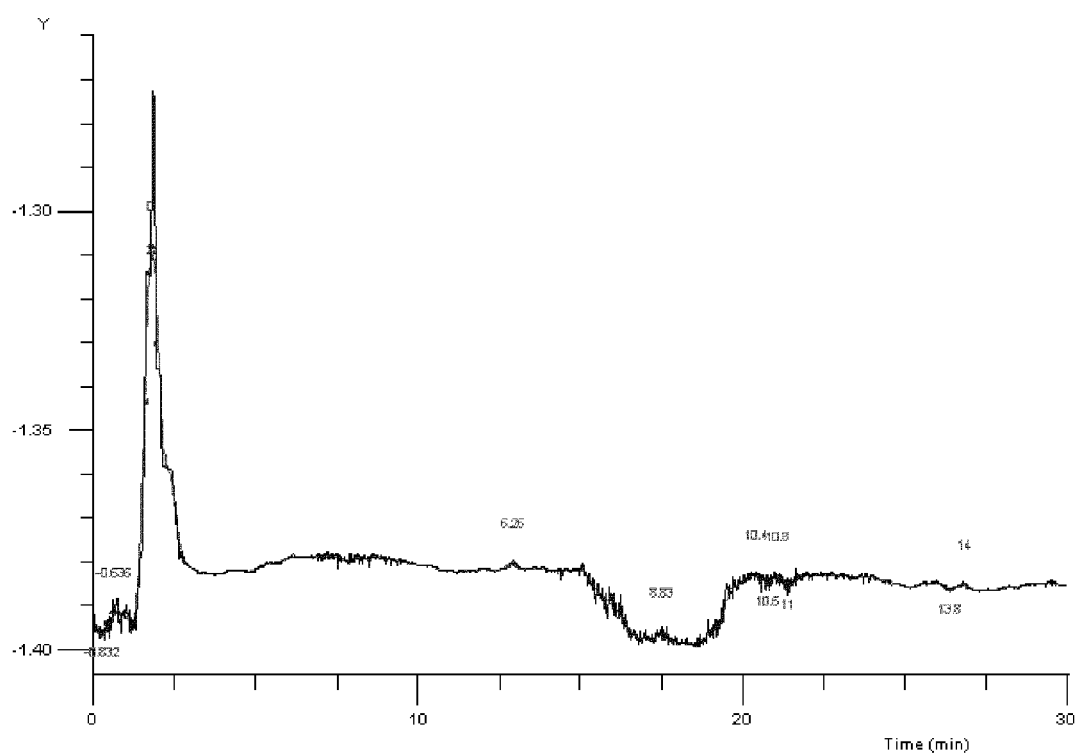
Figure 11: HPLC chromatogram of the aqueous extract of the root covering of Careya arborea

COMPOSITIONS AND METHODS CONTAINING NATURAL COMPOUNDS FROM NONCONVENTIONAL SOURCES THAT ARE USEFUL IN MAINTAINING NORMAL BLOOD SUGAR LEVELS

CROSS REFERENCE TO RELATED APPLICATIONS

This application claims foreign priority benefit of Indian Patent applications # 8542/MUM/2003, # 8543/MUM/2003, # 8541/MUM/2003, # 8540/MUM/2003 filed on May 28, 2003 at the Indian Patent Office, the disclosure of which is hereby incorporated by reference.

BACKGROUND OF INVENTION

Diabetes mellitus, commonly known as diabetes, is one of the world's oldest known diseases. In 1997, diabetes prevalence was introduced as a "basic health indicator" for member states by the WHO, which estimated in 1995 that the number of people with diabetes in the world would reach 300 million by 2025. The prevalence of diagnosed diabetes in the U.S. rose rapidly across all regions, demographic groups and in almost every state during the past decade. About 16 million people suffer from diabetes in the US alone, with an estimated 120 million sufferers worldwide. Diabetes was ranked as the seventh leading cause of death in the US, accounting for more than 300,000 premature deaths every year with about 800,000 new diabetes cases being diagnosed annually. Type II or non-insulin dependent diabetes accounts for most of these cases.

Diabetes mellitus is caused either by a lack of the hormone insulin (Type I diabetes) or the body's inability to use insulin (Type II diabetes also known as maturity-onset diabetes). Type II diabetes is often triggered by obesity, stress and a sedentary lifestyle. Diabetes is a chronic disorder characterized by high blood sugar levels and abnormal metabolism of carbohydrate, protein and fat. The disease is a result of the failure of the body to control blood sugar levels adequately. The normal fasting blood sugar levels are in the range of 75–115 mg/dL. After a meal, the body tightly regulates increases in blood sugar to a level not exceeding 180 mg/dL in people without diabetes.

Depending upon the nature of the disease, insulin and certain synthetic drugs like sulphonylureas, biguanidines and acarbose are widely used in its treatment. Careful management of diabetes, including control of high blood pressure, can delay some of the serious complications associated with the condition, which include eye diseases, disease of the peripheral blood vessels and kidney failure. In recent years, evidence of cases of "insulin resistance" and the occurrence of side effects from prolonged administration of conventional drugs have triggered the search for safe and effective alternatives. Several plant extracts and isolated phytochemicals have been examined for antidiabetic activity with a view to identify alternative treatment strategies for diabetes. It has been observed that certain resistant cases of diabetes that do not respond well to conventional drugs often respond well to supplementation with natural remedies.

The present invention describes compositions and methods containing the plant species *Flemingia macrophylla* and *Careya arborea* that are useful in maintaining normal blood sugar levels in humans and animals.

Metformin is an antihyperglycemic agent, which improves glucose tolerance in patients with type 2 diabetes, lowering both basal and postprandial plasma glucose. Its pharmacological mechanisms of action are different from other classes of oral antihyperglycemic agents. Metformin decreases hepatic glucose production, decreases intestinal absorption of glucose, and improves insulin sensitivity by increasing peripheral glucose uptake and utilization. Unlike sulfonylureas, metformin does not produce hypoglycemia in either patients with type 2 diabetes or normal subjects and does not cause hyperinsulinemia. With metformin therapy, insulin secretion remains unchanged while fasting insulin levels and day-long plasma insulin response may actually decrease. Metformin hydrochloride is a biguanide, which does not create any adverse effects on the metabolic reactions.

The presence of this metformin-like compund in the roots of *Flemingia macrophylla* and *Careya arborea* was confirmed using Micro HPLC.

The inventors are not aware of any prior art that describes specific compositions of *Flemingia macrophylla* and/or *Careya arborea* useful in maintaining normal blood sugar levels in humans and animals. The identity of the active principles therein that contribute to this effect has also not been elucidated before.

SUMMARY OF INVENTION

The invention describes compositions and methods containing nonconventional plant materials, and more particularly the species *Flemingia macrophylla* and *Careya arborea*, that help to maintain normal blood sugar levels in humans and animals. The method of preparation of such compositions and methods of quantifying active principles therein are also described. A Metformin-like compound were identified to be the active hypoglycemic principle in *Flemingia macrophylla* and *Careya arborea* root bark.

BRIEF DESCRIPTION OF DRAWINGS

FIG. 1 shows the blood glucose levels of the groups at different time intervals in the study with *Flemingia macrophylla* (bar graph).

FIG. 2 shows the blood glucose levels of the groups at different time intervals in the study with *Flemingia macrophylla* (line graph).

FIG. 3 shows the percent rise in blood glucose levels of the groups at different time intervals in the study with *Flemingia macrophylla* (bar graph).

FIG. 4 shows the percent increase in blood glucose levels of the groups at different time intervals in the study with *Flemingia macrophylla* (line graph).

FIG. 5 shows the blood glucose levels of the groups at different time intervals in the study with *Careya arborea* (bar graph).

FIG. 6 shows the blood glucose levels of the groups at different time intervals in the study with *Careya arborea* (line graph).

FIG. 7 shows the percent rise in blood glucose levels of the groups at different time intervals in the study with *Careya arborea*. (bar graph)

FIG. 8 shows the percent rise in blood glucose levels of the groups at different time intervals in the study with *Careya arborea* (line graph).

FIG. 9 shows the HPLC chromatogram of standard metformin hydrochloride.

FIG. 10 shows the HPLC chromatogram of the aqueous extract of the root covering of *Flemingia macrophylla*.

FIG. 11 shows the HPLC chromatogram of the aqueous extract of the root covering of *Careya arborea*.

DETAILED DESCRIPTION

EXAMPLE 1

*Flemingia macrophylla* Herbal Drug for Hypoglycemic Activity

Materials and methods: Root of Flemingia macrophylla was collected. The root cover (bark) was removed and dried under shade below 40° C. and powdered. Aqueous decoction Sample F-I was prepared by soaking the powdered root bark in 1% gum acacia solution overnight. The decoction was filtered to give Sample F-I. Sample F-II was freshly prepared by mixing the powdered root bark with 1% gum acacia solution, and used immediately for testing. The dose of drug in each case is 100 mg/kg body weight of the rats. Glucose solution (12.5 g/100 ml) was prepared in distilled water.

Normal albino rats were used for screening of natural product for hypoglycemic activity. At the primary screening level the natural product was fed to the animals orally. The dried sample powder as well as its aqueous extract was used. The blood glucose level was read in glucometer using Accutrend sensor comfort strip used in Advantage glucometer. The natural product was fed to the animal orally at a dose of 100 mg/kg body weight.

Fifteen Sprague Dawley strain (outbred) albino rats were taken and kept in polypropylene cages in three groups of three each for fifteen days for acclimatization under standard experimental room conditions.

On the sixteenth day all the food from each cage was removed and the animals were kept for overnight starvation (5:00 p.m. to 9:00 a.m.).

On seventeenth day, approximately 0.10 ml blood was drawn from tail end of each rat. This blood was introduced on the area specified on the strips for blood sample (Accutrend sensor comfort used in Advantage Glucometer). The strip was put in the glucometer for reading of blood sugar count. Animals, which showed blood glucose levels between 60 to 80 mg/dl, were finally selected and grouped into three and termed as Control Group, test sample treated groups F-I and F-II. Each group contained three rats.

Aqueous decoction sample F-I was prepared by soaking 0.5 g/3 ml, powdered sample overnight in distilled water in the night of day seventeen.

On day eighteen, glucose solution (12.5 g/100 ml) was prepared in distilled water. Aqueous solution of F-I was filtered. F-II was freshly prepared by adding 1 g sample/3 ml of water. Gum acacia solution was used as vehicle for oral administration of test samples to animal of group F-I and F-II at an arbitrary dose of 100 mg/kg body weight of the rats. The plant test samples were dissolved in 1% gum acacia solution (1 g/100 ml) in the ratio of 0.3 g in 3 ml. These doses were given with the help of 1.0 ml plastic syringe and cannula at zero hours. An equal amount of 1.0% acacia was given to animals of Control group immediately after drawing 0.10 ml blood from the tail end of each rat for glucose content (Zero hour sample). Table 1 gives the detailed account of body weight and dose of each group.

TABLE 1

Body weight and dosage data

| | Doses GROUP | | | | | | | | |
|---|---|---|---|---|---|---|---|---|---|
| | CONTROL GROUP | | | GROUP F I | | | GROUP F II | | |
| S. No. | Body wt. (gm) | Gum acacia (ml) | Glucose solution (ml) | Body wt. (gm) | Test sample (ml) | Glucose solution (ml) | Body wt. (gm) | Test sample (ml) | Glucose solution (ml) |
| 1 | 175 g | 0.5 | 1.4 | 175 | 0.5 | 1.4 | 125 | 0.25 | 1.0 |
| 2 | 175 g | 0.5 | 1.4 | 125 | 0.25 | 1.0 | 150 | 1.30 | 1.2 |
| 3 | 150 g | 0.3 | 1.2 | 175 | 0.5 | 1.4 | 150 | 1.30 | 1.2 |

Glucose solution was administered to animals of each group at a dose of 2.0 g/kg body weight, after 30 min of giving test samples. Approximately 0.10 ml blood was drawn from tail end of each rat at 30, 60, 90 and 120 min. Glucose content was determined for each animal with the help of Advantage Glucometer using Accutrend strips. No food was given to animal till the collection of last blood sample at 120 min. post glucose loaded. Tables 3 and 4 represent the blood glucose level of different groups at different time interval. The blood glucose levels at different time intervals are shown in FIGS. 1 and 2.

TABLE 2

Blood Glucose Level - Control Group

| S.No. | 0 min (mg/dl) | 30 min (mg/dl) | 60 min (mg/dl) | 90 min (mg/dl) | 120 min (mg/dl) |
|---|---|---|---|---|---|
| 1. | 56 | 86 | 69 | 73 | 80 |
| 2. | 58 | 127 | 79 | 104 | 69 |
| 3. | 60 | 99 | 80 | 76 | 66 |
| Mean ($X_i$) | 58 | 104 | 76 | 84.3 | 71.6 |

TABLE 3

Blood Glucose Level - Group (F-I)

| S.No. | 0 min (mg/dl) | 30 min (mg/dl) | 60 min (mg/dl) | 90 min (mg/dl) | 120 min (mg/dl) |
|---|---|---|---|---|---|
| 1. | 54 | 82 | 52 | 57 | 43 |
| 2. | 65 | 82 | 72 | 70 | 69 |
| 3. | 57 | 68 | 65 | 20 | 41 |
| Mean($X_i$) | 58.6 | 77.3 | 63 | 49 | 51 |

TABLE 4

Blood Glucose Level-Group (F II)

| S No. | 0 min (mg/dl) | 30 min (mg/dl) | 60 min (mg/dl) | 90 min (mg/dl) | 120 min (mg/dl) |
|---|---|---|---|---|---|
| 1. | 55 | 88 | 74 | 90 | 79 |
| 2. | 75 | 113 | 78 | 81 | 79 |
| 3. | 85 | 73 | 72 | 86 | 80 |
| Mean ($X_i$) | 71.6 | 91.3 | 74.6 | 85.6 | 79.3 |

TABLE 5

Statistical Analysis Of Control Group, Group F-I And Group F-II

| Groups | Blood Sugar ($X_i$) | Mean ($\overline{X}$) | $X_i - \overline{X}$ | Standard Deviation $\sigma = \sqrt{\sum_{x=1}^{5} \frac{(X_i - \overline{X})^2}{n}}$ |
|---|---|---|---|---|
| CONTROL GROUP | 58 | 78.78 | -20.78 | 15.21 |
| | 104 | | 25.22 | |
| | 76 | | -2.78 | |
| | 84.3 | | 5.52 | |
| | 71.6 | | -7.18 | |
| GROUP F I | 58.6 | 59.78 | -1.18 | 10.13 |
| | 77.3 | | 17.52 | |
| | 63 | | 3.52 | |
| | 49 | | -10.78 | |
| | 51 | | -8.78 | |
| GROUP F II | 71.6 | 80.48 | -8.88 | 7.18 |
| | 91.3 | | 10.82 | |
| | 74.6 | | -5.88 | |
| | 85.6 | | 5.12 | |
| | 79.3 | | -1.18 | |

TABLE 6

Mean + S.D. Of Control Group, Group F-I And Group F-II

| GROUPS | Rat No. | 0 min | 30 min | 60 min | 90 min | 120 min |
|---|---|---|---|---|---|---|
| CONTROL GROUP | 1 | 56 | 86 | 69 | 73 | 80 |
| | 2 | 58 | 127 | 79 | 104 | 69 |
| | 3 | 60 | 99 | 80 | 76 | 66 |
| MEAN ± SD | | 58 ± 15.21 | 104 ± 15.21 | 76 ± 15.21 | 84.3 ± 15.21 | 71.6 ± 15.21 |
| TEST SAMPLE GROUP F I | 4 | 54 | 82 | 52 | 57 | 43 |
| | 5 | 65 | 82 | 72 | 70 | 69 |
| | 6 | 57 | 68 | 65 | 20 | 41 |
| MEAN ± SD | | 58.6 ± 10.13 | 77.3 ± 10.13 | 63 ± 10.13 | 49 ± 10.13 | 51 ± 10.13 |
| TEST SAMPLE GROUP F II | 7 | 55 | 88 | 74 | 90 | 79 |
| | 8 | 75 | 113 | 78 | 81 | 79 |
| | 9 | 85 | 73 | 72 | 86 | 80 |
| MEAN ± SD | | 71.6 ± 7.18 | 91.3 ± 7.18 | 74.6 ± 7.18 | 85.6 ± 7.18 | 79.3 ± 7.18 |

TABLE 7

Percentage Rise In Blood Glucose Level At Particular Time

| Group | 30 min | 60 min | 90 min | 120 min |
|---|---|---|---|---|
| Control Group | 79.31 | 31.03 | 45.34 | 23.44 |
| Group F I | 31.91 | 7.50 | -16.38 | -12.96 |
| Group F II | 27.51 | 4.18 | 19.55 | 10.75 |

TABLE 8

Percent Antihyperglycaemic Activity of *Flemengia macrophylla*

| Value details | Control Group | Group FI | Group FII |
|---|---|---|---|
| Area under the curve | 5022 | 1711.2 | 1698.45 |
| % Anti hyperglycemic activity | — | −65.92 | −66.17 |

The percentage rise in blood glucose profile of post glucose loaded of rats in different groups at each time interval was determined from 0 min value (Table 7) as follows:

$$\% \text{ Rise in blood glucose} = \left( \frac{\text{Blood glucose level at determining time period}}{\text{Blood glucose level at 0 min time period}} \times 100 \right) - 100$$

The area under each curve for control and test groups was also determined (FIG. 4).

$$\% \text{ Anti hyperglycemic activity} = \left[ \frac{\text{Area under curve of test sample plant drug treated group}}{\text{Area under curve of control group}} \times 100 \right] - 100$$

The control group showed a considerable increase at thirty minutes compared to the two test groups. At sixty minute the blood glucose level lowered down in all the line groups. As per the figure at ninety minutes, the level increased in control group and Group FII, whereas the decrease in blood glucose level in Group F-I was very much apparent. No considerable change was observed in the groups at 120 minutes of the experiment. Statistical treatment was done for the observed values of blood glucose level at different time interval (Tables 5 and 6). Percent rise in blood glucose level was calculated (Table 7).

The two test groups FI and FII showed marked hypoglycemic activity (FIGS. 3 and 4). Percent inhibition in post prandial hypoglycemia by test sample plant drug was calculated as per the adopted standard method (Table 8). Test Group FI showed 65.92% antihyperglycemic activity, and Test Group FII gives 66.17% antihyperglycemic activity. The experiments prove that the plant species have antihyperglycemic property. At the same time hypoglycemia was not observed in any of the experimental animals.

The effect of the herbal drug is more pronounced when used in powdered form in the doses standardized as described. It was found that the effect of the doses persisted after a fortnight. No indication of hypoglycemia (low blood sugar) was observed in any of the experimental animals.

Conclusions: *Flemingia macrophylla* root cover powder and aqueous decoction of the root cover powder showed hypoglycemic activity in glucose loaded albino rats. Hypoglycemia was not observed in any of the experimental animals, proving it to be a safe drug. Use of aqueous decoction of powdered froot cover of *Flemingia macrophylla* or its aqueous decoction in standardized formulations is a safe and effective method for treating abnormal blood sugar levels.

EXAMPLE 2

A method of Making *Careya arborea* Herbal Drug for Complex Hyperglycemic and Hypoglycemic Activity Materials and Methods: Root of *Careya arborea* was collected. The root cover was removed and dried under shade below 40° C. and powdered. Aqueous decoction sample C-I was prepared by soaking the sample in 1% gum acacia overnight and in the next morning it was filtered and used for testing. Sample C-II freshly prepared by adding sample in 1% gum acacia for immediate use. Gum acacia solution was used as vehicle for oral administration of test samples to animal of group C-I and C-II. The dose of drug in each case is 100 mg/kg body weight of the rats. Glucose solution (12.5 g/100 ml) was prepared in distilled water.

Normal albino rats were used for screening of natural product for hypoglycemic activity. At the primary screening level, the natural product was fed to the animals orally. The dried sample powder as well as its aqueous extract has been used. Animals were fasted for sixteen hours. The blood from tail end of each rat was withdrawn for estimating blood glucose level. The blood glucose level was read in glucometer using Accutrend sensor comfort strip used in Advantage glucometer. The natural product was fed to the animal orally and a dose of 100 mg/kg body weight was used.

Fifteen Sprague Dawley strain (out bred) albino rats were taken and kept in polypropylene cages in three groups of three each for fifteen days for acclimatization under standard experimental room conditions.

On the sixteenth day all the food from each cage was removed and the animals were kept for overnight starvation (5:00 p.m. to 9:00 a.m.).

On the eighteenth day, glucose solution (12.5 g/100 ml) was prepared in distilled water. Aqueous solution sample C-I was filtered. Sample C-II was freshly prepared by adding 1 g powder/3 ml of water. Gum acacia solution was used as vehicle for oral administration of test samples to animals of group C-I and C-II at an arbitrary dose of 100 mg/kg body weight of the rats. The plant test samples were dissolved in 1% gum acacia solution (1 g/100 ml) in the ratio of 0.3 g in 3 ml. These doses were given with the help of 1.0 ml plastic syringe and cannula at zero hours. An equal amount of 1.0% gum acacia was given to animals of Control group immediately after drawing 0.10 ml blood from the tail end of each rat for glucose content (Zero hour sample). Table 9 gives the detailed account of body weight and dose of each group.

TABLE 9

DOSES

| | CONTROL GROUP | | | GROUP C I | | | GROUP C II | | |
|---|---|---|---|---|---|---|---|---|---|
| S. No | Body Wt. (gm) | Gum acacia sample (ml) | Glucose solution (ml) | Body wt. (gm) | Test sample (ml) | Glucose solution (ml) | Body wt.(g) | Test sample (ml) | Glucose solution (ml) |
| 1 | 175 | 0.5 | 1.4 | 125 | 0.25 | 1.0 | 150 | 0.3 | 1.2 |
| 2 | 175 | 0.5 | 1.4 | 250 | 0.5 | 2.0 | 125 | 0.25 | 1.0 |
| 3 | 150 | 0.3 | 1.2 | 150 | 0.3 | 1.2 | 200 | 0.4 | 1.6 |

TABLE 10

Blood Glucose Level - Control Group

| | Time | | | | |
|---|---|---|---|---|---|
| S.No. | 0 min (mg/dl) | 30 min (mg/dl) | 60 min (mg/dl) | 90 min (mg/dl) | 120 min (mg/dl) |
| 1 | 56 | 86 | 69 | 73 | 80 |
| 2 | 58 | 127 | 79 | 104 | 69 |
| 3 | 60 | 99 | 80 | 76 | 66 |
| Mean | 58 | 104 | 76 | 84.3 | 71.6 |

TABLE 11

Blood Glucose Level - Group C-I

| | Time | | | | |
|---|---|---|---|---|---|
| S.No. | 0 min (mg/dl) | 30 min (mg/dl) | 60 min (mg/dl) | 90 min (mg/dl) | 120 min (mg/dl) |
| 1 | 57 | 89 | 71 | 70 | 64 |
| 2 | 64 | 97 | 84 | 80 | 91 |
| 3 | 54 | 68 | 64 | 56 | 49 |
| Mean | 59.3 | 84.6 | 73 | 68.6 | 68 |

TABLE 12

Blood Glucose Level - Group C-II

| | Time | | | | |
|---|---|---|---|---|---|
| S.No. | 0 min (mg/dl) | 30 min (mg/dl) | 60 min (mg/dl) | 90 min (mg/dl) | 120 min (mg/dl) |
| 1 | 56 | 59 | 70 | 87 | 80 |
| 2 | 60 | 97 | 104 | 86 | 103 |
| 3 | 58 | 168 | 175 | 84 | 85 |
| Mean | 58 | 108 | 116.3 | 85.6 | 89.3 |

TABLE 13

Statistical Analysis Of Control Group, Group C-I And Group C-II

| GROUPS | MEAN Xi | $\overline{X}$ | Xi − $\overline{X}$ | STANDARD DEVIATION $\sigma = \sqrt{\sum_{x=1}^{5} \frac{(Xi - \overline{X})^2}{n}}$ |
|---|---|---|---|---|
| Control group | 58 | 78.78 | −20.78 | 15.21 |
| | 104 | | 25.22 | |
| | 76 | | −2.78 | |
| | 84.3 | | 5.52 | |
| | 71.6 | | −7.18 | |
| Group C-I | 59.3 | 70.7 | −11.4 | 8.16 |
| | 84.6 | | 13.9 | |
| | 73 | | 2.3 | |
| | 68.6 | | −2.1 | |
| | 68 | | −2.7 | |
| Group C-II | 58 | 91.44 | −33.44 | 20.24 |
| | 108 | | 16.56 | |
| | 116.3 | | 24.86 | |
| | 85.6 | | −5.84 | |
| | 89.3 | | −2.14 | |

TABLE 14

Mean ± S.D. Of Control Group, Group C-I And Group C-II

| GROUPS | Rat No. | BLOOD GLUCOSE LEVEL (mg/dl) | | | | |
|---|---|---|---|---|---|---|
| | | 0 min | 30 min | 60 min | 90 min | 120 min |
| Control group | 1 | 56 | 86 | 69 | 73 | 80 |
| | 2 | 58 | 127 | 79 | 104 | 69 |
| | 3 | 60 | 99 | 80 | 76 | 66 |
| MEAN ± SD | | 58 ± 15.21 | 104 ± 15.21 | 76 ± 15.21 | 84.3 ± 15.21 | 71.6 ± 15.21 |

TABLE 14-continued

Mean ± S.D. Of Control Group, Group C-I And Group C-II

| GROUPS | Rat No. | BLOOD GLUCOSE LEVEL (mg/dl) | | | | |
|---|---|---|---|---|---|---|
| | | 0 min | 30 min | 60 min | 90 min | 120 min |
| Group C-I | 4 | 57 | 89 | 71 | 70 | 64 |
| | 5 | 64 | 97 | 84 | 80 | 91 |
| | 6 | 54 | 68 | 64 | 56 | 49 |
| MEAN ± SD | | 59.3 ± 8.16 | 84.6 ± 8.16 | 73 ± 8.16 | 68.6 ± 8.16 | 68 ± 8.16 |
| Group C-II | 7 | 56 | 59 | 70 | 87 | 80 |
| | 8 | 60 | 97 | 104 | 86 | 103 |
| | 9 | 58 | 168 | 175 | 84 | 85 |
| MEAN ± SD | | 58 ± 20.24 | 108 ± 20.24 | 116.3 ± 20.24 | 85.6 ± 20.24 | 89.3 ± 20.24 |

TABLE 15

Percent Rise In Blood Glucose Level At Particular Time

| Group | Time | | | |
|---|---|---|---|---|
| | 30 min | 60 min | 90 min | 120 min |
| Control group | 79.31 | 31.03 | 45.34 | 23.44 |
| Group C-I | 42.66 | 23.10 | 15.68 | 14.67 |
| Group C-II | 86.20 | 100.51 | 47.58 | 53.96 |

% Rise in blood glucose profile of post glucose loaded of rats in different groups of each time interval was determined from 0 min value, as follows:

$$\% \text{ Rise in blood glucose} = \left( \frac{\text{Blood glucose level at determining time period}}{\text{Blood glucose level at 0 min time period}} \times 100 \right) - 100$$

The area under each curve was determined (from FIG. 8). Percent inhibition in post parandial hyperglycemia by test sample was calculated as follows:

$$\% \text{ Anti hyperglycemic activity} = \left[ \frac{\text{Area under curve of test sample plant drug treated group}}{\text{Area under curve of control group}} \times 100 \right] - 100$$

TABLE 16

| Value details | Anti-hyperglycemic activity | | |
|---|---|---|---|
| | Control group | Test sample Group C I | Test sample Group C II |
| Area under the curve | 5022 | 2663.25 | 7838.1 |
| % Anti hyperglycemic activity | — | −46.96 | 56.07 |

Group C-I and Group C-II were administered with aqueous decoction of the sample powder and powdered sample respectively The results on blood glucose levels are shown in FIG. 5 and FIG. 6 and tabulated in Tables 10–12. Test Group C I showed effective lowering of the blood glucose level (hypoglycemic effect), but, surprisingly the Test Group CII showed increase in blood glucose level (hyperglycemic effect) (Tables 11, 12). Statistical treatment was done for the observed values of blood glucose level at different time interval (Tables 13 and 14). Percent rise in blood glucose level was calculated (Table 15). Percent antihyperglycemic activity was calculated as per the standard method for both the test groups (Table 16). The percent rise in blood sugar levels shown in FIGS. 7 and 8 clearly indicates the complex hyperglycemic and hypoglycemic activity of *Careya arborea*.

The effect of herbal drug is more pronounced when used in powdered form itself in the doses standardized as described. It was found that the effect of the doses given still persisted after a fortnight.

This species showed complex hyperglycemic and hypoglycemic activity in glucose loaded albino rats. Hypoglycemia was not observed in any of the experimental animals, proving it to be a safe drug.

EXAMPLE 3

An Improved Micro HPLC Method for Identification of Metformin Hydrochloride in Root of *Flemingia Macrophylla*

Micro High Pressure Liquid Chromatography was the method employed. Large reduction in solvent consumption and therefore solvent operation and toxic waste disposal cost, very low flow rates used with microcolumns make it the method of choice for HPLC-MS, particularly the benchtop MS with electrospray and nanospray interfaces.

Low flow rates used in microcolumns facilitate the unified approach to chromatography. These major advantages are the result of the fact, that small particles, such as 3 and 5 µm can be efficiently packed in microcolumn and therefore same separation chemistry and elution pattern as that obtained from a 4.6 mm id, column can be expected. As a result of smaller column diameters for microcolumn HPLC, the flow rate requirement is also reduced and the elution peak volume (flow rate times peak width at half-height) is therefore reduced by a factor equal to the ratio of the cross-sectional areas for the 4.6 mm to the microcolumns.

The stationary phase bonded to a porous polymer is held in a narrow bore stainless steel column and the liquid mobile phase is forced through under considerable pressure with the help of a suitable pumping system. The mobile phase is a miscible solvent mixture. The compounds are monitored as they elute off the column by means of a detector, usually measuring in the ultra violet or visible regions of the spectrum.

HPLC was Carried Out Under Following Conditions

| Column | Octadecyl silane (ODS) C-18/15 cm. |
|---|---|
| Particle size | 3 micrometer |
| Inner diameter of column | 5 mm |
| Mobile phase | 50:50, Water:Methanol |
| Wave length | 220 nm |
| Flow rate | 0.2 ml/min. |
| Instrument used | TSP (Thermo Separation Product) make micro HPLC system with UV-VIS detector. |

Materials and Methods: HPLC Grade water and methanol from E Merck India, Standard Solution: Aqueous solution of metformin hydrochloride (0.1666 mg/ml) was used as standard. Test Sample of *Flemingia macrophylla:* 500 mg. of sample powder was submerged in 3 ml distilled water. After keeping for 6 hours, it was stirred for 30 min, filtered and the solution diluted 20 times.

The chromatograms obtained during HPLC Studies are represented in FIGS. 9 and 10. The retention time and characteristic peak was recorded. The standard samples were run in micro HPLC under the similar conditions as described. The test samples were also run under the same experimental conditions.

For both the test samples peaks were observed at the same retention time, This confirms the presence of the same compound metformin hydrochloride or metformin-like compound in the test sample. Thus with the help of micro HPLC, a new method has been evolved to determine the presence of an inherent natural compound in the herbal preparation having the same pharmacological effect as synthetic metformin hydrochloride.

Metformin hydrochloride is a synthetic compound used in synthetic drugs for the treatment of diabetes. An identical compound was found to be naturally present in the root cover of *Flemingia macrophylla.*

EXAMPLE 4

An Improved Micro HPLC Method for Identification of Metformin Hydrochloride in Root of *Careya Arborea*

Micro High Pressure Liquid Chromatography was the method employed. Large reduction in solvent consumption and therefore solvent operation and toxic waste disposal cost, very low flow rates used with micro-columns make it the method of choice for HPLC-MS, particularly the benchtop MS with electrospray and nanospray interfaces. Low flow rates used in micro-columns facilitate the unified approach to chromatography. These major advantages are the result of the fact that small particles such as 3 and 5 μm can be efficiently packed in micro column and therefore same separation chemistry and elution pattern as that obtained from a 4.6 mm id column can be expected. As a result of smaller column diameters for micro-column HPLC, the flow rate requirement is also reduced and the elution peak volume (flow rate times peak width at half-height) is therefore reduced by a factor equal to the ratio of the cross-sectional areas for the 4.6 mm to the micro-columns.

The stationary phase bonded to a porous polymer is held in a narrow bore stainless steel column and the liquid mobile phase is forced through under considerable pressure with the help of a suitable pumping system. The mobile phase is a miscible solvent mixture. The compounds are monitored as they elute off the column by means of a detector, usually measuring in the ultra violet or visible regions of the spectrum.

HPLC was carried out under following conditions:

| Column | Octadecyl silane (ODS) C-18/15 cm. |
|---|---|
| Particle size | 3 micrometer |
| Inner diameter of column | 5 mm |
| Mobile phase | 50:50, Water:Methanol |
| Wave length | 220 nm |
| Flow rate | 0.2 ml/min. |
| Instrument used | TSP (Thermo Separation Product) make micro HPLC system with UV-VIS detector. |

Materials and methods: HPLC Grade water and methanol from E Merck India, Standard Solution: Aqueous solution of Metformin hydrochloride (0.166 mg/ml) was used as standard. Test Sample of *Careya arborea:* 500 mg. of sample powder was submerged in 3 ml distilled water. After keeping for 6 hours, it was stirred for 30 min, filtered and the solution was diluted 20 times.

The chromatograms obtained during HPLC studies are represented in FIGS. 9 and 11. The retention time and characteristic peak was recorded. The standard samples were run in micro HPLC under the similar conditions already mentioned. The test samples were also run under the same experimental conditions. For both the test samples peaks were observed at the same retention time. This confirms the presence of the same compound metformin hydrochloride or metformin-like compound in the test sample. Thus with the help of micro HPLC, a new method has been evolved to determine the presence of an inherent natural compound in the herbal preparation having the same pharmacological effect as synthetic metformin hydrochloride.

Metformin hydrochloride is a synthetic compound used in synthetic drugs for the treatment of diabetes. An identical compound was found to be naturally present in the root cover of *Careya arborea.*

The invention claimed is:

1. A method of making Flemingia macrophylla herbal drug composition with hypoglycemic activity, comprising the following steps:
   (1) collecting Flemingia macrophylla root material including root bark and removing the root bark;
   (2) drying the root bark in shade below 40° C.;
   (3) grinding the root bark to a fine powder and;
   (4) mixing the dried root powder with 1% gum acacia solution to obtain aqueous drug composition, or soaking the dried root bark powder in 1% gum acacia aqueous solution for 12 to 17 hours, followed by filtration to obtain aqueous drug composition.

* * * * *